(12) United States Patent
Suh et al.

(10) Patent No.: US 11,065,034 B2
(45) Date of Patent: Jul. 20, 2021

(54) MODULAR AUTOMATIC HAIR IMPLANTER

(71) Applicants: Electronics and Telecommunications Research Institute, Daejeon (KR); Kyungpook National University Industry-Academic Cooperation Foundation, Daegu (KR)

(72) Inventors: Jung Wook Suh, Daegu (KR); Kyu Hyung Kim, Daegu (KR); Moon Kyu Kim, Daegu (KR); Jung Chul Kim, Daegu (KR); Tae Wuk Bae, Daegu (KR); Soo In Lee, Daejeon (KR); Eun Chang Choi, Daegu (KR)

(73) Assignees: Electronics and Telecommunications Research Institute, Daejeon (KR); Kyungpook National University Industry-Academic Cooperation Foundation, Daegu (KR)

( * ) Notice: Subject to any disclaimer, the term of this patent is extended or adjusted under 35 U.S.C. 154(b) by 218 days.

(21) Appl. No.: 16/287,566

(22) Filed: Feb. 27, 2019

(65) Prior Publication Data
US 2019/0262036 A1 Aug. 29, 2019

(30) Foreign Application Priority Data
Feb. 28, 2018 (KR) .................. 10-2018-0024134
Jan. 18, 2019 (KR) .................. 10-2019-0007050

(51) Int. Cl.
*A61B 17/34* (2006.01)
*A61B 17/00* (2006.01)

(52) U.S. Cl.
CPC ............ *A61B 17/3468* (2013.01); *A61B 2017/00398* (2013.01); *A61B 2017/00752* (2013.01)

(58) Field of Classification Search
CPC ...... A61B 17/3468; A61B 2017/00752; A61B 2017/00398
See application file for complete search history.

(56) References Cited

U.S. PATENT DOCUMENTS

| | | | |
|---|---|---|---|
| 5,611,811 A * | 3/1997 | Goldberg | A61B 17/3468 606/187 |
| 8,152,827 B2 * | 4/2012 | Oostman, Jr. | A61F 2/10 606/187 |
| 8,211,134 B2 * | 7/2012 | Oostman, Jr. | A61B 34/37 606/187 |
| 9,848,909 B2 | 12/2017 | Bae et al. | |
| 2016/0045223 A1 | 2/2016 | Kim et al. | |

FOREIGN PATENT DOCUMENTS

| KR | 10-2000-0065685 A | 11/2000 |
|---|---|---|
| KR | 10-2017-0012697 A | 2/2017 |
| KR | 10-2018-0001374 A | 1/2018 |

\* cited by examiner

*Primary Examiner* — Julian W Woo
(74) *Attorney, Agent, or Firm* — Rabin & Berdo, P.C.

(57) ABSTRACT

An automatic hair implanter is capable of continuously performing hair transplantation work by applying a structure of a conventional manual hair implanter. The automatic hair implanter (hair transplantation device) comprises a rotating magazine therein, and several needle modules are stored in the magazine. Two pushrods, which are positioned on a rear portion of the device and capable of translational motion, play a role of pushing a needle and a shaft, which constitute a needle module, forward. The needle and the shaft may be moved backward by a spring positioned inside the magazine.

14 Claims, 9 Drawing Sheets

MODULAR AUTOMATIC HAIR IMPLANTER

CROSS-REFERENCE TO RELATED APPLICATION

This application claims priority to and the benefit of Korean Patent Applications No. 2018-0024134 filed on Feb. 28, 2018 and No. 2019-0007050 filed on Jan. 18, 2019, the disclosure of which is incorporated herein by reference in its entirety.

BACKGROUND

1. Field of the Invention

The present disclosure relates to a modular automatic hair implanter, and more particularly, to a modular automatic hair implanter capable of continuously performing hair transplantation work by improving a structure of a conventional manual hair implanter.

2. Discussion of Related Art

When hair implantation is performed, there is a method of collecting hair follicles using a strip method and implanting the hair follicles using a manual hair implanter. In the collection of the hair follicles, the strip method extracts a strip of scalp in a patient's occipital region in a long shape, stitches the occipital region, and then separates the extracted strip into hair follicular units. On the other hand, a follicular unit extraction (FUE) method is a non-incision method in which a thin punching machine is used to extract the hair follicles directly from the scalp.

A hair implantation method may mainly be divided into two methods, which are a method using a manual hair implanter and a method using tweezers.

A method in which a small slit is made in an implant area at which hair implantation is required and a hair follicle (hair) is directly pushed into a slit hole using tweezers is mainly used in western countries. On the other hand, in a method using a manual hair implanter, which is widely used domestically (in Korea), there is no need to provide a separate slit, and a hair follicle is not pressed while being planted, and thus it may be seen as a more advanced form of hair implantation method.

FIG. 1 illustrates a process of planting a hair follicle (hair) using a conventional hair implanter 10. In a process of pulling out a needle 12, an operator person lifts a body 18 (a grip part or a needle assembly) of the hair implanter 10 using remaining his/her fingers while pushing a rear end part (a shaft assembly) 16 of a shaft 14 with his/her index finger. The shaft assembly 16 is in a fixed state with the shaft 14, and the body (needle assembly) 18 is in a fixed state with the needle 12. A compression spring 20 is provided between the shaft assembly 16 and the needle assembly 18 and plays a role of moving the shaft 14 relatively backwards from the needle 12.

However, the process of lifting the body of the hair implanter and pulling out the needle in a state in which the index finger is fixed requires repeated practice. In addition, when a height of the index finger is not properly maintained in the process of pulling out the needle, a height of the shaft which pushes the hair follicle may be changed so as to cause the hair follicle to come out of the scalp or be inserted too deeply. When the hair follicle planted as described above is not planted at a proper height, the scalp becomes uneven and in the worst case the planted hair follicle dies and hair does not grow.

SUMMARY OF THE INVENTION

The present disclosure is directed to providing a modular automatic hair implanter capable of simplifying movement of a hand necessary for hair transplantation work and simultaneously allowing the hair transplantation work to be continuously performed.

According to an aspect of the present disclosure, there is provided a modular automatic hair implanter including a needle module in which a hair follicle is accommodated, a magazine in which the needle module is mounted, and an operating unit configured to press the needle module mounted in the magazine to insert the hair follicle into a scalp.

The magazine may comprise a module slit mounted in a circumferential direction thereof, the needle module being mounted in each module slit, and the operating unit may rotate the magazine and press the hair follicle accommodated in the needle module positioned in a predetermined position to insert the hair follicle into the scalp.

Configurations and operations of the present disclosure described above will be more apparent by referring to detailed embodiments described below in detail in connection with the accompanying drawings.

BRIEF DESCRIPTION OF THE DRAWINGS

The above and other objects, features, and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

The above and other advantages, features, and a scheme for the advantages of the present disclosure will become readily apparent with reference to the following detailed description when considered in conjunction with the accompanying drawings. However, the scope of the present disclosure is not limited to such embodiments, and the present disclosure may be realized in various forms. The embodiments to be described below are only embodiments provided to complete the disclosure of the present disclosure and assist those skilled in the art to completely understand the scope of the present disclosure. The present disclosure is defined only by the description of the appended claims.

Meanwhile, terms used herein are used to aid in the explanation and understanding of the present disclosure and are not intended to limit the scope spirit of the present disclosure. As used herein, the singular forms "a," "an," and "the" are intended to include the plural forms as well, unless the context clearly indicates otherwise. It will be understood that the terms "comprise" or "comprising" when used herein, specify some stated components, steps, operations and/or elements, but do not preclude the presence or addition of one or more other components, steps, operations and/or elements.

Hereinafter, a preferred embodiment of the present disclosure will be described in detail with reference to the accompanying drawings.

Referring to FIGS. 2 to 12, a modular automatic hair implanter 100 comprises a needle module 200, a magazine 300, and an operating unit 400.

Figure 4:
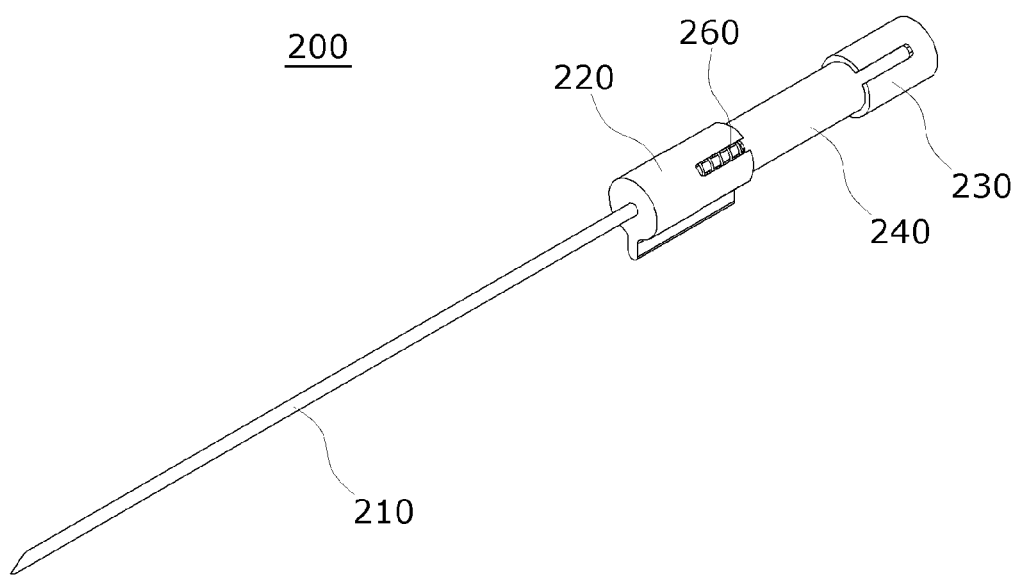
FIGS. 4 and 5 are a perspective view and a cross-sectional view of a needle module constituting the modular automatic hair implanter according to the present disclosure.
Figure 5:
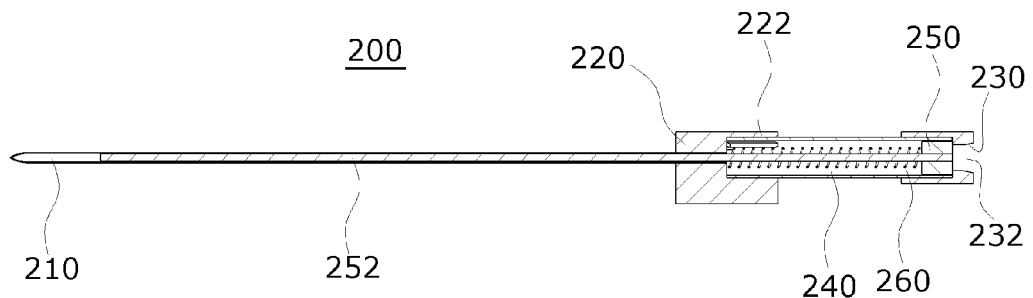

Referring to FIGS. 4 and 5, the needle module 200 comprises a needle 210, a needle front block 220, a needle rear block 230, a housing case 240, a shaft block 250, and an inner spring 260.

Here, the needle 210 and the needle front block 220 are configured to be separated so as to allow the needle 210 and the needle front block 220, which are non-recyclable after use, to be discarded; and to allow the needle rear block 230, the housing case 240, the shaft block 250, and the inner spring 260, which are recyclable after use, to be sterilized.

Further, after the needle module 200 is assembled, the needle 210, the needle front block 220, the needle rear block 230, the housing case 240, the shaft block 250, and the inner spring 260 are integrally operated.

In the needle module 200, the needle 210 and the needle front block 220; the needle rear block 230 and housing case 240; and a shaft 252 and the shaft block 250 may each be integrally formed. Alternatively, in the needle module 200, the needle 210 and the needle front block 220, and the housing case 240 may be integrally formed.

The needle 210 has a certain length and is formed in a hollow shape to accommodate a hair follicle. An end portion of the needle 210 is formed to be inclined for allowing smooth insertion. That is, due to the inclined end portion, the needle 210 may be smoothly inserted and the hair follicle accommodated therein may be discharged therefrom.

The needle front block 220 is coupled to a rear side of the needle 210. Further, the needle front block 220 has a rear side at which a mounting groove 222 is formed so that the housing case 240 may be coupled thereto. That is, the needle front block 220 supports the rear side of the needle 210, and the housing case 240 is supported by the mounting groove 222.

The needle rear block 230 is disposed to be spaced apart from the needle front block 220. Further, the needle rear block 230 has a mounting groove 232 formed therein. That is, the needle rear block 230 is disposed to be spaced apart from the needle front block 220 by a length of the housing case 240 and supports the housing case 240 together with the needle front block 220 through the mounting groove 232 of the needle rear block 230.

The housing case 240 has a certain length and is formed in a hollow shape. That is, the housing case 240 formed in the hollow shape supports the inner spring 260.

The shaft block 250 is mounted to the needle rear block 230. Also, the shaft 252 configured to discharge the hair follicle positioned in the needle 210 to the outside is mounted on a front side of the shaft block 250. That is, the shaft block 250 is mounted on the mounting groove 232 of the needle rear block 230 and moves forward or backward according to an operation of the operating unit 400 to discharge the hair follicle positioned inside the needle 210 to the outside.

The inner spring 260 is mounted inside the housing case 240. In addition, both side ends of the inner spring 260 are supported by the needle front block 220 and the needle rear block 230 so that the shaft block 250 is returned to an original position thereof while maintaining a constant tension.

Figure 6:
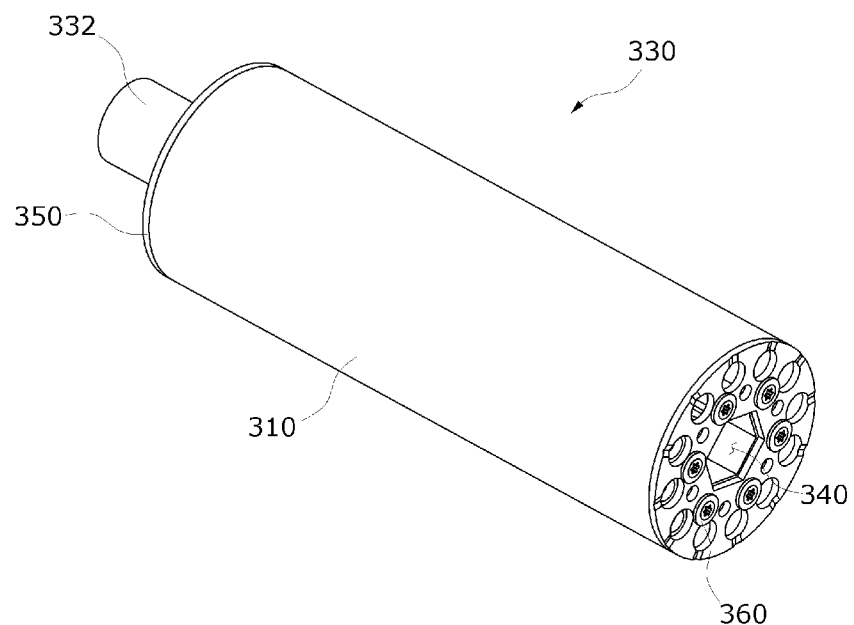
FIG. 6 is a perspective view illustrating a magazine of the modular automatic hair implanter according to the present disclosure.

Next, referring to FIG. 6, the magazine 300 roughly comprises a magazine case 310, a magazine body 320 therein, a magazine front side part 330, a magazine front plate 350, a magazine rotating part 340, and a magazine rear plate 360.

The magazine case 310 is formed in a cylindrical shape. That is, the magazine case 310 is formed to have a certain diameter and length to accommodate therein the magazine body 320, the magazine front side part 330, and the magazine rotating part 340.

The magazine body 320 is located inside the magazine case 310. The magazine body 320 has a rotation mounting hole 321 formed at a center thereof and a module slit 322 mounted at an edge thereof in a circumferential direction (see FIG. 3). That is, the magazine body 320 has the rotation mounting hole 321, which is formed at the center thereof so that the magazine body 320 may be rotated according to an operation of the magazine front side part 330 and the magazine rotating part 340. The magazine body 320 further has the module slit 322, to which the needle module 200 is mounted in a circumferential direction about the rotation mounting hole 321. In this case, an outer spring 270 is mounted in the module slit 322.

Further, the magazine front plate 350 is mounted on a front side of the magazine body 320 to support a magazine front side part 330 and a position of the needle module 200; and a magazine rear plate 360 is mounted on a rear side of the magazine body 320 to support the magazine rotating part 340 and the position of the needle module 200.

The magazine front side part 330 is mounted on the front side of the magazine body 320. Here, the magazine front side part 330 may be mounted to the magazine body 320 by means of an insertion-coupled structure other than any fastening device.

Figure 7:
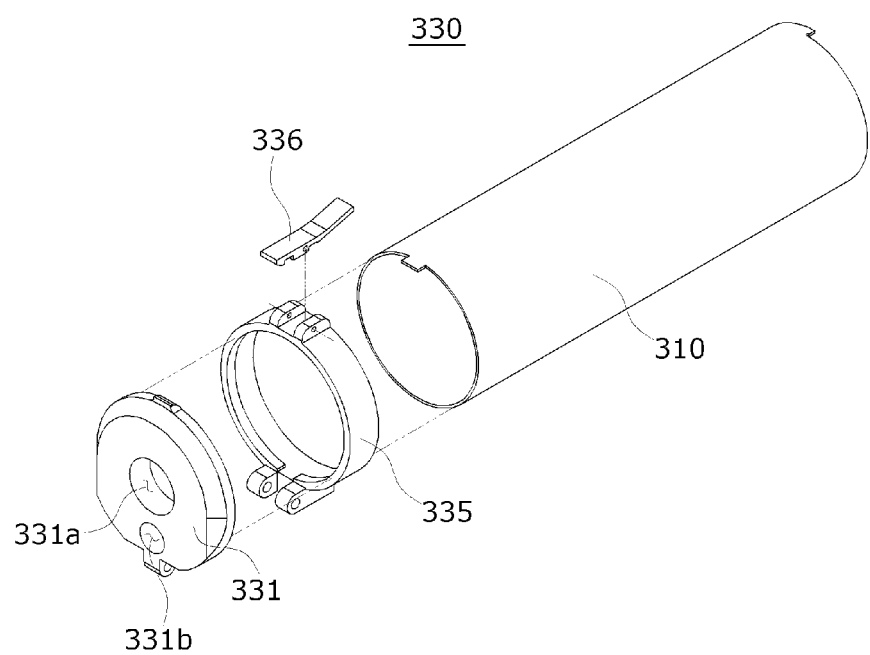
FIG. 7 is a configuration diagram of the magazine constituting the modular automatic hair implanter according to the present disclosure excluding a magazine body.
Figure 8:
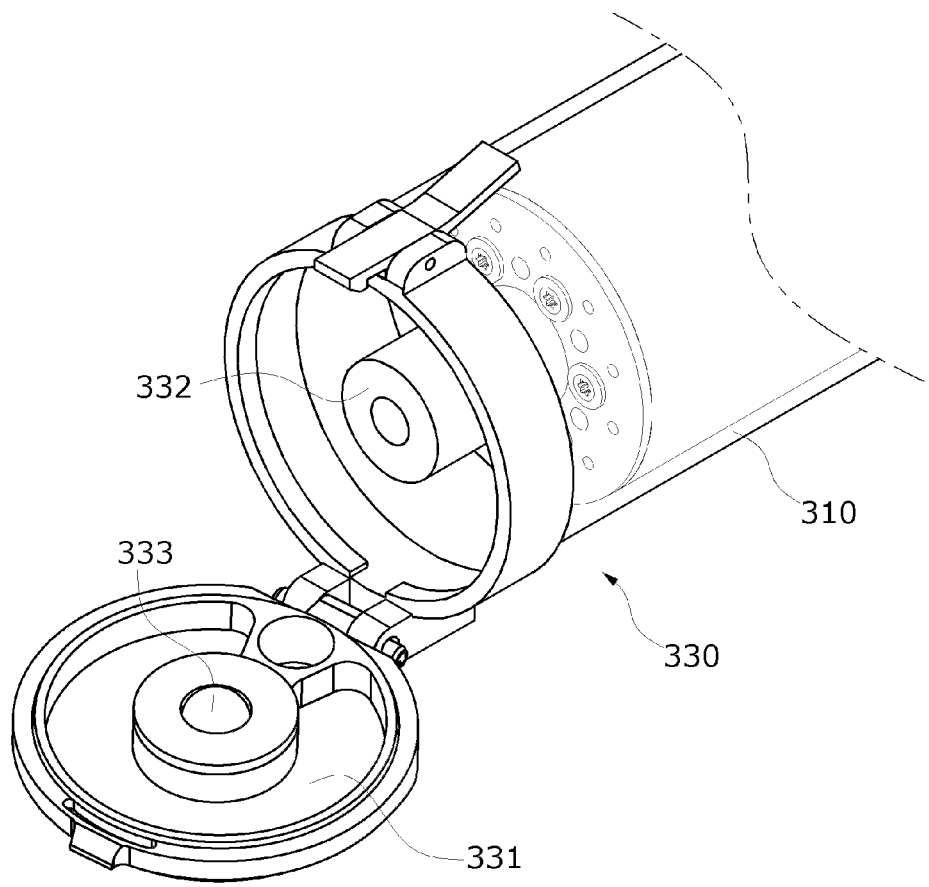
FIG. 8 is a perspective view illustrating an operating state of a front side part of the magazine constituting the modular automatic hair implanter according to the present disclosure.
Figure 9:
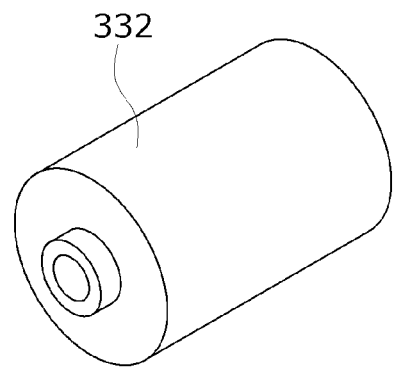
FIGS. 9 and 10 are perspective views each illustrating a rotation shaft and a rotating part of the magazine constituting the modular automatic hair implanter according to the present disclosure.
Figure 10:
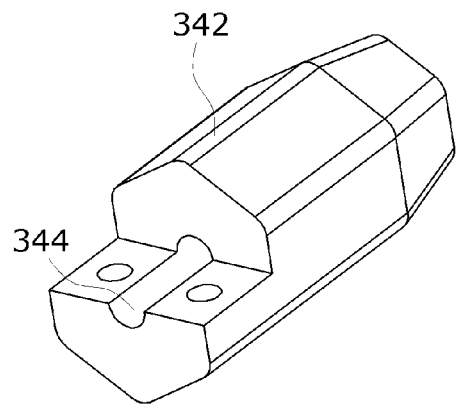
Figure 11:
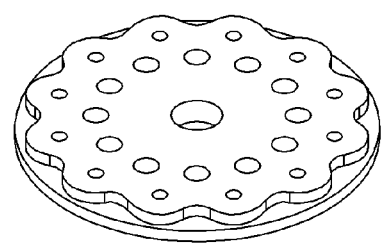
FIGS. 11 and 12 are perspective views each illustrating a front plate and a rear plate of the magazine constituting the modular automatic hair implanter according to the present disclosure.
Figure 12:
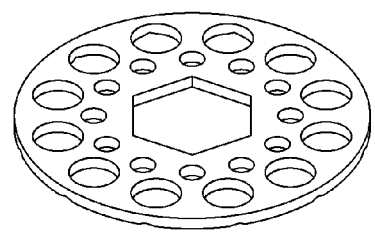
Figure 13:
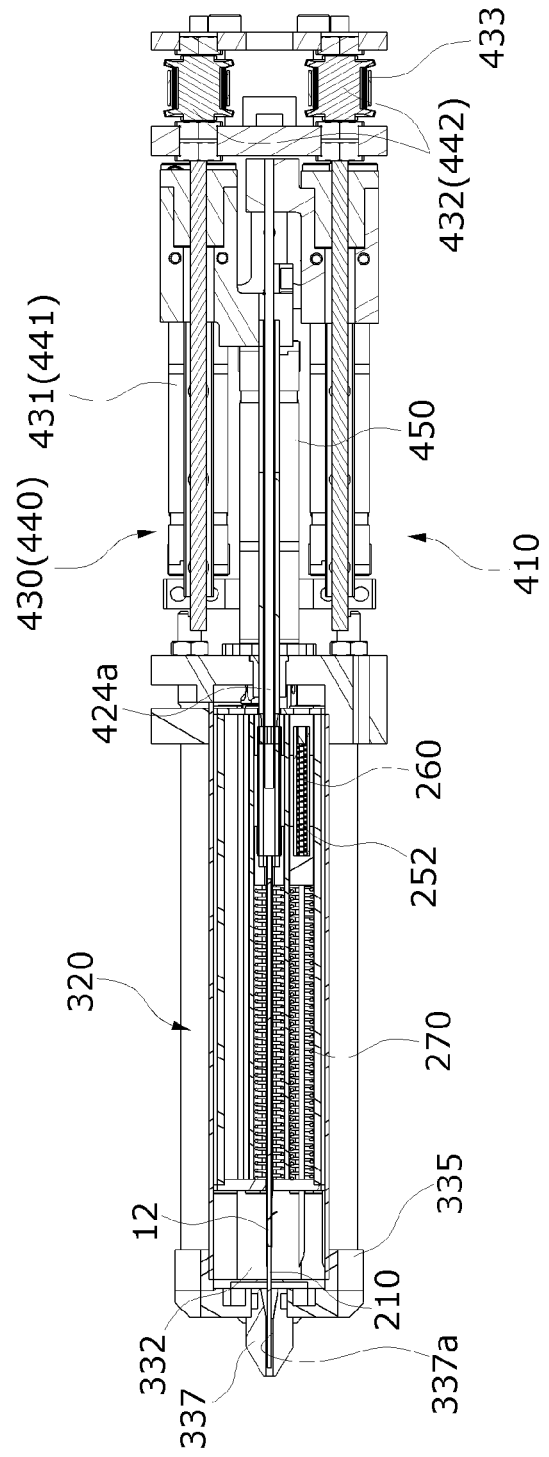
FIGS. 13 to 15 are views illustrating operating states of the modular automatic hair implanter according to the present disclosure.
Figure 14:
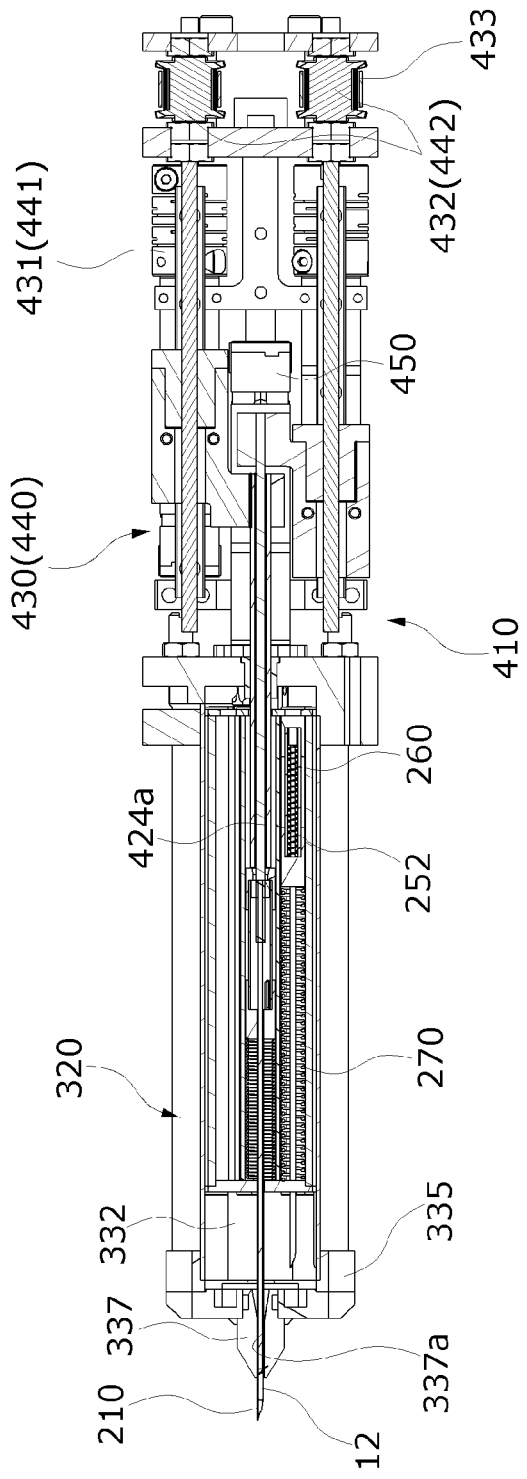
Figure 15:
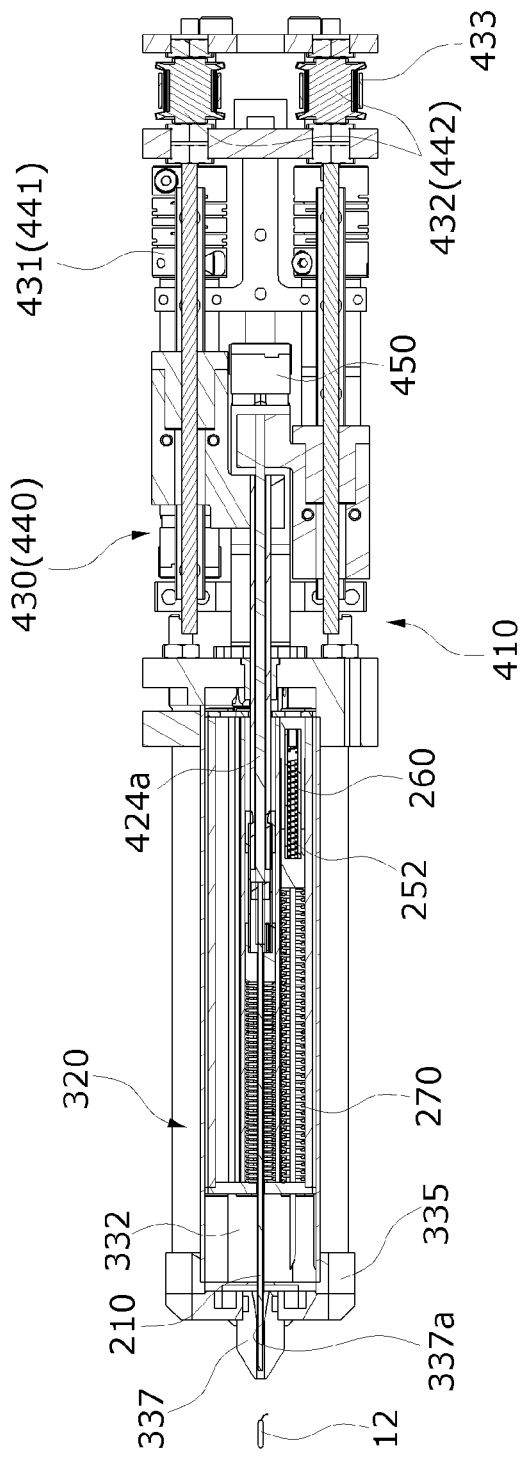

In addition, the magazine front side part 330 comprises a front lid 331 formed in a circular disk shape (see FIG. 7). The front lid 331 has a shaft mounting hole 331a formed at a central portion thereof, and at least one through hole 331b which is a portion corresponding to the module slit 322. Referring to FIG. 8, the magazine front side part 330 further comprises a ball roller 333 mounted in the shaft mounting hole 331a, and a rotation shaft 332 having one end supported by the ball roller 333 of the shaft mounting hole 331a and the other end fixed to the magazine body 320.

In FIG. 7, the front lid 331 may be mounted on one side of the hinge 335 to open or close an inside of the magazine front side part 330, and an elastic fixture 336 configured to fix or separate the front lid 331 may be mounted on a side opposite to the one side. That is, the front lid 331 is rotated about the one side of the hinge 335 according to an operation of the elastic fixture 336, thereby opening or closing a front side of the magazine body 320.

A needle guide port 337 having a guide hole 337a formed at a center thereof (see FIGS. 2 and 3) may be mounted on the through hole 331b of the front lid 331 to guide a position of the needle 210 discharged from the needle module 200.

Referring to FIG. 6, the magazine rotating part 340 is mounted on the rear side of the magazine body 320. In detail, see FIG. 10, the magazine rotating part 340 comprises a rotating body 342 formed in a polygonal shape and a shaft mounting groove 344 formed in a center of a rear side of the rotating body 342. That is, the magazine rotating part 340 is coupled to the magazine body 320 and the magazine rear plate 360, and rotates the magazine body 320 using a rotational force transmitted from the operating unit 400.

Figure 1:
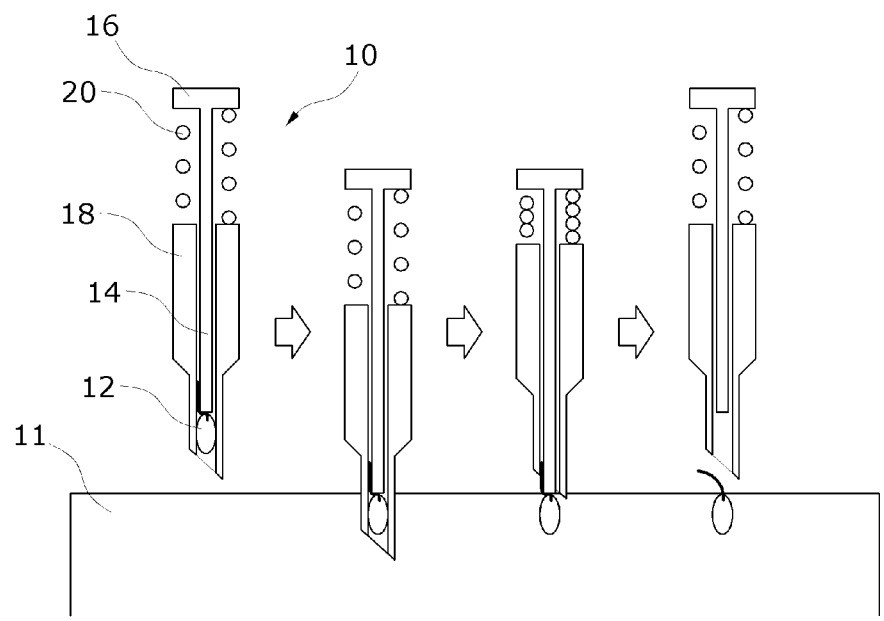
FIG. 1 is a view illustrating a process of planting a hair follicle using a conventional hair implanter.
Figure 2:
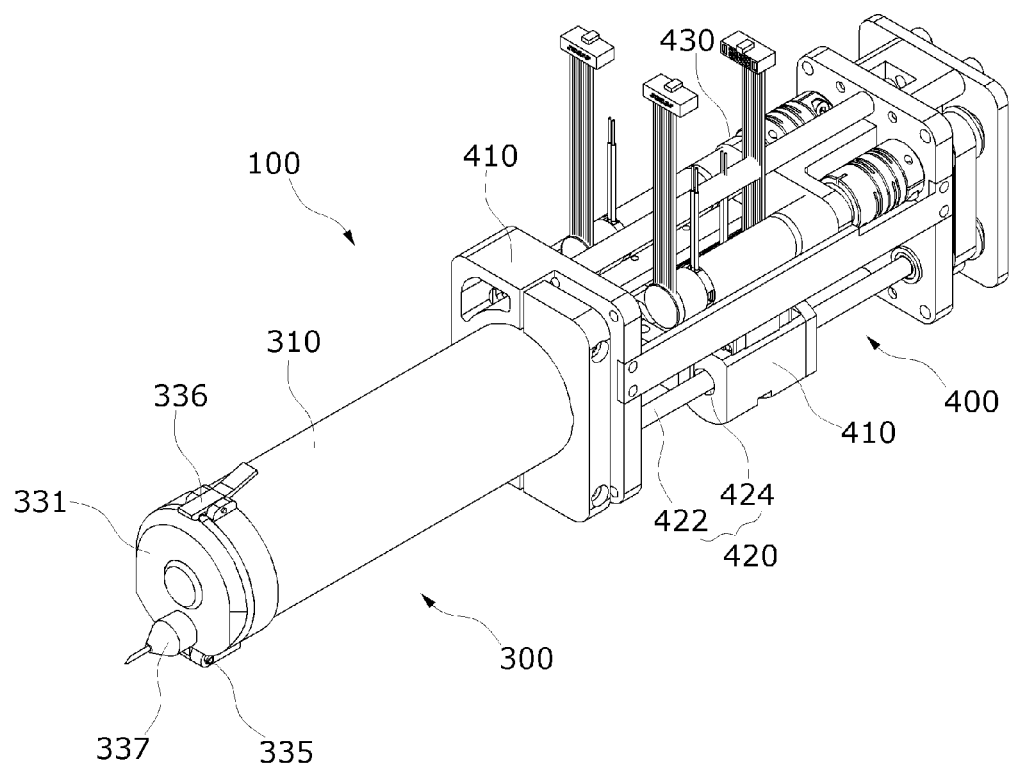
FIGS. 2 and 3 are a perspective view and a cross-sectional view of a modular automatic hair implanter according to the present disclosure.
Figure 3:
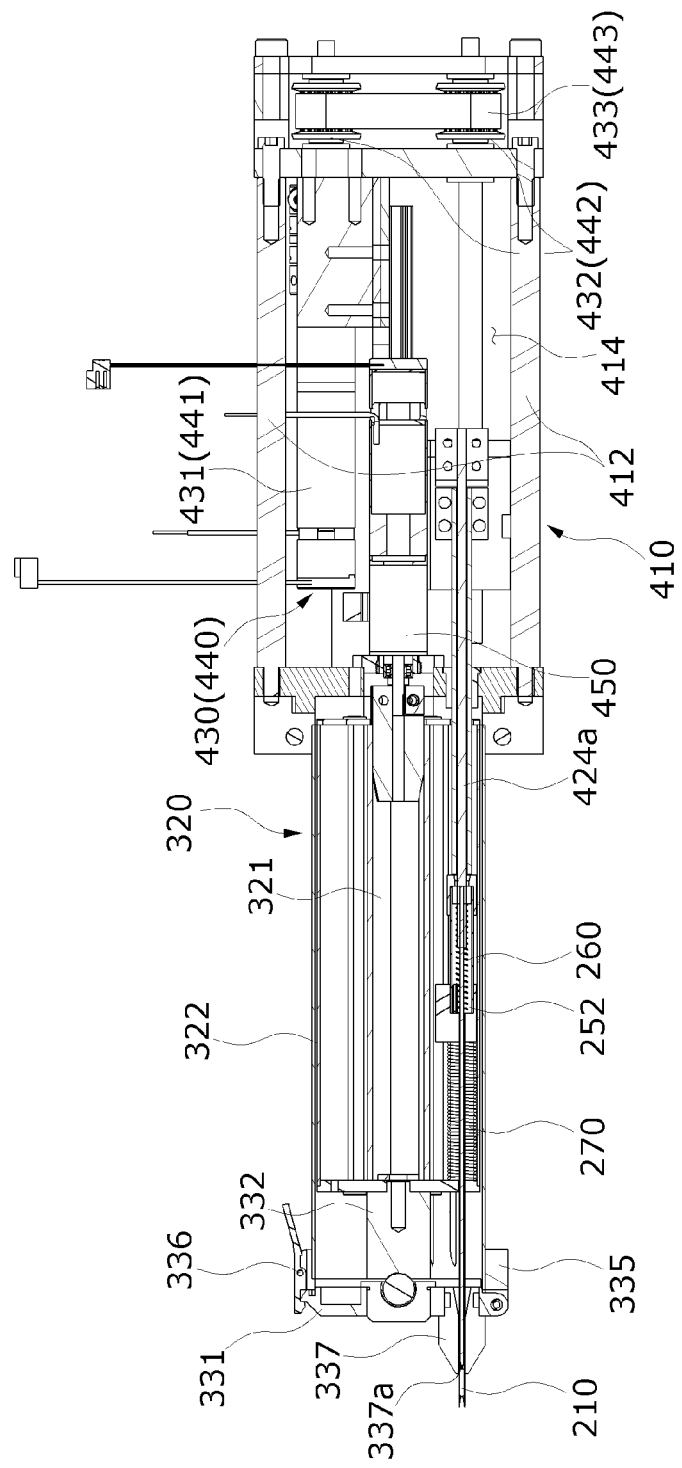

Next, regarding FIGS. 2 and 3, the operating unit 400 comprises a housing 410, an operating part 420, an operation driving part 430, a needle operating part 440, and a magazine operating part 450.

The housing 410 is formed by combining a plurality of frames 412. That is, the housing 410 combines the plurality of frames 412 according to an environment and purpose and forms an accommodation space 414 therein.

The operating part 420 is mounted in the accommodation space 414 of the housing 410. Here, an example in which the operating part 420 is mounted in a lower portion of the accommodation space 414 is described.

The operating part 420 comprises a ball screw 422 formed with a certain length and a transport operation port 424 which is moving forward or backward along the ball screw 422 and configured to press the shaft block to discharge the hair follicle mounted in the needle to the outside. That is, in the operating part 420, the transport operation port 424 moves forward or backward along the ball screw 422 according to an operation of the operation driving part 430 and the needle operating part 440.

Here, a transporting bar 424a is mounted on the transport operation port 424 to move the shaft block 250 forward.

The operation driving part 430 is mounted in the accommodation space 414 of the housing 410. Here, an example in which the operation driving part 430 is mounted on an upper portion of the accommodation space 414 is described.

The operation driving part 430 comprises a motor 431, and a pulley 432 and a timing belt 433, which are configured to transfer a rotational force of the motor 431 to the operating part 420. Here, it is obvious that a pulley is also mounted on the ball screw 422 of the operating part 420 corresponding to the pulley 432.

That is, the operation driving part 430 transfers the rotational force of the motor 431 to the ball screw 422 through the pulley 432 and the timing belt 433 to move the transport operation port 424 backward or forward.

The needle operating part 440 is mounted in the accommodation space 414 of the housing 410. Here, an example in which the needle operating part 440 is mounted on the upper portion of the accommodation space 414 is described.

Further, the needle operating part 440 comprises a motor 441, and a pulley 442 and a timing belt 443, which are configured to transfer a rotational force of the motor 441 to the operating part 420. Here, it is obvious that a pulley is also mounted on the ball screw 422 of the operating part 420 corresponding to the pulley 442.

That is, the needle operating part 440 transfers the rotational force of the motor 441 to the ball screw 422 through the pulley 442 and the timing belt 443 to move the transport operation port 424 backward or forward.

In more detail, after the operation of the operation driving part 430, the needle operating part 440 moves the transport operation port 424 forward so that the transport operation port 424 discharges the hair follicle accommodated in the needle 210 to the outside.

The magazine operating part 450 is mounted in the accommodation space 414 of the housing 410. In addition, a rotation shaft of the magazine operating part 450 is mounted in the shaft mounting groove 344 of the magazine rotating part 340 (see FIG. 10).

That is, the magazine operating part 450 comprises a motor and rotates the magazine rotating part 340 to rotate the needle module 200 so that the needle module 200 is positioned at a designated position. Here, it may be effective that the motor constituting the magazine operating part 450 comprises a stepping motor capable of disposing the needle module 200 at a predetermined position.

Next, the automatic hair implanter from a viewpoint of assembling each of the modules described above will be described below.

First, a plurality of needle modules 200 are formed, wherein the needle module 200 comprises a needle 210 having a hollow shape; a needle front block 220 to which the needle 210 is coupled and which has a mounting groove 222 formed at the rear side thereof; a needle rear block 230 disposed to be spaced apart from the needle front block 220 and having a mounting groove 232 formed therein; a housing case 240 having both side ends which are respectively inserted into and coupled to the mounting groove 222 of the needle front block 220 and the mounting groove 232 of the needle rear block 230; a shaft block 250 mounted to the needle rear block 230 and having a front side to which a shaft 252 configured to discharge the hair follicle positioned in the needle 210 to the outside is mounted; and an inner spring 260 mounted in the housing case 240 and having both ends supported by the needle front block 220 and the needle rear block 230.

Meanwhile, in the needle module 200, both ends of the housing case 240 may be respectively inserted into and coupled to the mounting groove 222 of the needle front block 220 and the mounting groove 232 of the needle rear block 230 but may be coupled thereto with various coupling methods such as an adhesive-coupling method or a screw-coupling method as long as both ends of the housing case 240 may be firmly coupled to the mounting groove 222 of the needle front block 220 and the mounting groove 232 of the needle rear block 230.

Next, a magazine 300 is mounted, wherein the magazine 300 comprises a magazine case 310 having a cylindrical shape; a magazine body 320 mounted inside the magazine case 310 and having a rotation mounting hole 321 formed at the center thereof and having a module slit 322 formed on the edge thereof in a circumferential direction; and a magazine front side part 330 mounted in the front side of the magazine body 320 and having an edge portion in which a needle discharging through hole 331b is formed so that the needle 210 discharged from the needle module 200 mounted on the module slit 322 may be discharged to the outside.

Here, the magazine front side part 330 comprises a front lid 331 formed in a circular plate shape and having a shaft mounting hole 331a formed at the central portion thereof and at least one through hole 331b which is at a portion corresponding to the module slit 322, a ball roller 332 mounted in the shaft mounting hole 331a, and a rotation shaft 333 having one end supported by the ball roller 332 of the shaft mounting hole 331a and the other end fixed to the magazine body 320.

In addition, the preparation work of the modular automatic hair implanter 100 is completed by mounting the operating unit 400 on the rear side of the magazine 300, wherein the operating unit 400 comprises: a housing 410; an operating part 420 mounted in the housing 410 and including a ball screw 422 formed with a certain length and a transport operation port 424 which moves backward or forward along the ball screw 422 to press a shaft block to discharge the hair follicle mounted in the needle to the outside; an operation driving part 430 connected to the ball screw 422 of the operating part 420 to move the transport operation port 424 backward and forward by a predetermined section; a needle operating part 440 connected to the ball screw 422 of the operating part 420 and configured to move the transport operation port 424 forward to discharge the hair follicle accommodated in the needle to the outside according to the operation of the operation driving part 430; and a magazine operating part 450 mounted in the housing 410 to rotate the magazine 300.

Now, an operation sequence of the assembled modular automatic hair implanter will be described below.

First, the needle 210 is mounted on the needle module 200. The magazine rotating part 340 of the magazine 300 is detached, and then the outer spring 270 and the needle module 200 are mounted on the module slit 322. Then, the magazine rotating part 340 is attached.

Thereafter, the housing case 240 is detached from the needle rear block 230. The magazine body 320 to which the needle module 200 is coupled, the housing case 240 and the like are sterilized, and then the housing case 240 is attached to the needle rear block 230.

Thereafter, each hair follicle is mounted on each needle 210. The front lid 331 constituting the magazine front side part 330 is opened, and the magazine body 320 is mounted on the magazine case 310.

Subsequently, an operation position of the magazine body 310 is set up by operating the magazine operating part 450. Then, an operation signal is transmitted to the operating unit 400 in a state in which the needle guide port 337 of the modular automatic hair implanter 100 is brought into close contact with a position (scalp of a patient) where the hair is to be planted. Here, operation means of the operating unit 400 is started and stopped by a known button or controller switch mounted on one side of the housing 410.

Thereafter, the operation driving part 430 transfers the rotational force of the motor 431 to the ball screw 422 through the pulley 432 and the timing belt 433 to move the transport operation port 424 forward.

Here, the motor 441 rotates at a speed and distance similar to those of the motor 431 of the operation driving part 430 so that the needle operating part 440 brings the transporting bar 424a into close contact with a rear end of the shaft block 250.

Further, after the operation of the operation driving part 430, the needle operating part 440 moves forward the transport operation port 424 so that the transport operation port 424 discharges the hair follicle accommodated in the needle 210 to the scalp.

Next, the operation driving part 430 and the needle operating part 440 are operated to position the needle 210 and the transport operation port 424 in initial states thereof, and then the magazine body 320 is rotated through the magazine operating part 450. Thereafter, operations described above are repeatedly performed.

Subsequently, when the operation of the modular automatic hair implanter 100 is completed, the needle guide port 337 is removed from the scalp, and the magazine body 320 and the needle module 200 are separated. Afterward, the process of mounting a new needle module 200 to the magazine body 320 is performed repeatedly.

When a modular automatic hair implanter according to the present disclosure is used, a user's task is to bring a nozzle of a front side part of the hair implanter into close contact with a desired implantation position and move the position of the nozzle by several millimeters for a next hair transplantation work. Further, an automatic hair implanter of the present disclosure can be stably operated without malfunction due to a relatively simple structure, be continuously operated by using a plurality of needle modules, and drastically reduce the size of a grip part.

While the present disclosure has been particularly described with reference to exemplary embodiments, it will be understood by those skilled in the art that various changes in form and details may be made without departing from the spirit and scope of the present disclosure. Therefore, the embodiments of the present disclosure are not intended to limit but are intended to illustrate the technical idea of the present disclosure, and the scope of the technical idea of the present disclosure is not limited by the embodiments. The scope of the present disclosure shall be construed on the basis of the accompanying claims in such a manner that all of the technical ideas included within the scope equivalent to the claims belong to the present disclosure.

What is claimed is:

1. A modular automatic hair implanter comprising:
   a needle module configured to accommodate a hair follicle;
   a magazine in which the needle module is mounted; and
   an operating unit configured to press the needle module mounted in the magazine to insert the hair follicle into a scalp, wherein the needle module comprises:
   a needle having a hollow shape;
   a needle front block to which the needle is coupled and having a mounting groove formed at a rear side thereof;
   a needle rear block disposed to be spaced apart from the needle front block and having a mounting groove formed therein;
   a housing case having both side ends respectively coupled to the mounting groove of the needle front block and the mounting groove of the needle rear block;
   a shaft block mounted to the needle rear block and having a front side to which a shaft configured to discharge the hair follicle positioned in the needle to ihfc-an outside is mounted; and
   an inner spring mounted in the housing case and having both side ends supported by the needle front block and the needle rear block.

2. The modular automatic hair implanter of claim 1, wherein the needle and the needle front block, the needle rear block and the housing case, and the shaft and the shaft block are each integrally formed.

3. The modular automatic hair implanter of claim 1, wherein the needle and the needle front block are integrally formed with the housing case.

4. The modular automatic hair implanter of claim 1, wherein the needle front block and the housing case are integrally formed with the needle rear block.

5. A modular automatic hair implanter comprising:
a needle module, comprising a needle having a hollow shape, configured to accommodate a hair follicle;
a magazine in which the needle module is mounted; and
an operating unit configured to press the needle module mounted in the magazine to insert the hair follicle into a scalp, wherein the magazine comprises;
a magazine case having a cylindrical shape;
a magazine body mounted in the magazine case and having a rotation mounting hole formed at a center thereof and a module slit formed on an edge thereof in a circumferential direction, the needle module being mounted in the module slit;
a magazine front side part mounted on a front side of the magazine body and having a needle discharge hole formed an edge portion thereof so that the needle discharged from the needle module mounted on the module slit is discharged to an outside; and
a magazine rotating part mounted on a rear side of the magazine body and configured to rotate the magazine body using a rotational force transmitted from the operating unit,
wherein the magazine front side part comprises a front lid having a circular plate shape and formed with at least one through hole, which is a portion corresponding to the module slit, and a rotation shaft having one end supported by the front lid and another end fixed to the magazine body.

6. The modular automatic hair implanter of claim 5, further comprising a magazine front plate and magazine rear plate,
wherein the magazine front plate is mounted on the front side of the magazine body to support the magazine front side part and a position of the needle module,
wherein the magazine rear plate is mounted on the rear side of the magazine body to support the magazine rotating part and the position of the needle module.

7. The modular automatic hair implanter of claim 5, wherein a shaft mounting hole is formed at a center of the front lid, and a ball roller is mounted on the shaft mounting hole to support the one end of the rotation shaft.

8. The modular automatic hair implanter of claim 5, wherein the front lid comprises a hinge to open or close an inside of the magazine front side part.

9. The modular automatic hair implanter of claim 8, wherein the front lid further comprises an elastic fixture mounted on the opposite side of the hinge to fix or separate the front lid.

10. The modular automatic hair implanter of claim 5, wherein a needle guide port having a guide hole formed at a center thereof is mounted in the through hole of the front lid.

11. A modular automatic hair implanter comprising:
a needle module, comprising a needle having a hollow shape, configured to accommodate a hair follicle;
a magazine in which the needle module is mounted; and
an operating unit configured to press the needle module mounted in the magazine to insert the hair follicle into a scalp, wherein the operating unit comprises:
a housing;
an operating part mounted in the housing, and including a ball screw formed with a certain length and a transport operation port which moves forward or backward along the ball screw and presses a shaft block to discharge the hair follicle accommodated in the needle to an outside;
an operation driving part connected to the ball screw of the operating part and configured to move the transport operation port backward and forward by a predetermined section;
a needle operating part connected to the ball screw of the operating part and configured to move the transport operation port forward to discharge the hair follicle accommodated in the needle to the outside according to operation of the operation driving part; and
a magazine operating part mounted in the housing and configured to rotate the magazine.

12. The modular automatic hair implanter of claim 11, wherein the magazine operating part comprises a motor.

13. The modular automatic hair implanter of claim 11, wherein the operation driving part comprises a motor, and a pulley and a timing belt, which are configured to transfer a rotational force of the motor to the operating part.

14. The modular automatic hair implanter of claim 11, wherein the needle operating part comprises a motor, and a pulley and a timing belt, which are configured to transfer a rotational force of the motor to the operating part.

* * * * *